(12) United States Patent
Patil

(10) Patent No.: US 6,540,916 B2
(45) Date of Patent: Apr. 1, 2003

(54) ANTIMICROBIAL SINTERED POROUS PLASTIC FILTER

(75) Inventor: Arvind S. Patil, Davidson, NC (US)

(73) Assignee: Microban Products Company, Huntersville, NC (US)

( * ) Notice: Subject to any disclaimer, the term of this patent is extended or adjusted under 35 U.S.C. 154(b) by 0 days.

(21) Appl. No.: 09/946,025

(22) Filed: Sep. 4, 2001

(65) Prior Publication Data

US 2002/0033365 A1 Mar. 21, 2002

Related U.S. Application Data (63) Continuation-in-part of application No. 09/181,358, filed on Oct. 28, 1998, now Pat. No. 6,283,308, which is a continuation-in-part of application No. 08/877,080, filed on Jun. 17, 1997, now Pat. No. 5,868,933, which is a continuation-in-part of application No. 08/573,067, filed on Dec. 15, 1995, now Pat. No. 5,762,797.

(51) Int. Cl.[7] .................................................. B01D 39/00
(52) U.S. Cl. ................ 210/502.1; 210/490; 210/500.36
(58) Field of Search ........................ 210/501.1, 500.36, 210/490; 264/41, 126; 55/523, 524; 428/323; 424/400; 119/709, 28.5

(56) References Cited

U.S. PATENT DOCUMENTS

| | | | |
|---|---|---|---|
| 4,797,243 A | | 1/1989 | Wolbrom ..................... 264/126 |
| 5,547,481 A | | 8/1996 | Herding et al. ............... 55/523 |
| 6,004,667 A | * | 12/1999 | Sakurada et al. |
| 6,030,558 A | | 2/2000 | Smith et al. .................. 264/41 |
| 6,093,407 A | * | 7/2000 | Cummings et al. |
| 6,196,156 B1 | * | 3/2001 | Denesuk et al. |
| 6,238,575 B1 | * | 5/2001 | Patil |
| 6,240,874 B1 | * | 6/2001 | Denesuk et al. |
| 2002/0033365 A1 | * | 3/2002 | Patil |

FOREIGN PATENT DOCUMENTS

| EP | 0659482 A1 | 6/1995 |
|---|---|---|
| EP | 0743085 A2 | 11/1996 |

* cited by examiner

*Primary Examiner*—Ana Fortuna
(74) *Attorney, Agent, or Firm*—Dougherty, Clements & Hofer (57) ABSTRACT

An improved sintered porous thermoplastic filter incorporating a second thermoplastic treated with a non-leaching antimicrobial agent for the purification of liquids. The method of making the filter is also disclosed.

10 Claims, 8 Drawing Sheets

PRIOR ART

ANTIMICROBIAL SINTERED POROUS PLASTIC FILTER

CROSS REFERENCE TO RELATED APPLICATIONS

This application is a continuation-in-part of U.S. patent application Ser. No. 09/181,358, filed Oct. 28, 1998, now U.S. Pat. No. 6,283,308, which is a continuation-in-part of U.S. patent application Ser. No. 08/877,080 filed Jun. 17, 1997, now U.S. Pat. No. 5,868,933, which is a continuation-in-part of U.S. patent application Ser. No. 08/573,067, filed Dec. 15, 1995, which issued as U.S. Pat. No. 5,762,797 on Jun. 9, 1998.

FIELD OF THE INVENTION

The present invention relates to filters for the purification of liquids. In particular the invention relates to the production and antimicrobial treatment of sintered porous thermoplastic filters used for the purification of liquids, for the protection of such filters from microbial growth and for the purification of liquids treated by them with respect to microbial and other dissolved and undissolved contaminants.

BACKGROUND OF THE INVENTION

Sintered porous filters made from thermoplastic materials are used extensively in treating potable water and other fluids to remove particulate and dissolved contaminants. (See U.S. Pat. No. 6,030,558; U.S. Pat. No. 4,797,243; U.S. Pat. No. 5,547,481; EPO Patent 743,085A2; and EPO Patent Application 659,482A1) Sintering is a process of compressing powdered thermoplastics in a mold at temperatures just below their melting point. Powdered particles are fused together but the mass, as a whole does not melt. These sintered materials are used as filters since they can be made to have specific porosity. These filters are typically made by fusing discrete particles of selected thermoplastic polymers under elevated temperature and pressure conditions while enclosed in a mold. These thermoplastic polymers typically have a low melt flow rate, which means that at their melting point they have a very high viscosity which minimizes the flow of the melted mass. When heated, the polymer particles fuse at the point of contact, creating a solidified porous body with a complex pore structure and with good mechanical strength. It is necessary that the particles retain their shape, save for the slight softening at the point of contact where fusing occurs as the temperature is reduced from the elevated temperatures to near ambient levels. Particle shape retention can occur only when the melt flow rate of the polymer is low. The melt flow rate is defined by the so-called Melt Index, which is a measure of the amount of material that is extruded from a small orifice during a period of 10 minutes at 43.5 psi of pressure. Sintering temperatures of 374 F. (190 C.) and 446 F. (230 C.) are specified for polyethylene and polypropylene respectively. (ASTM Method-D-1238). A high melt index material indicates a low-viscosity polymer. Melt Index is calculated and given as grams per 10 min. Low melt index is usually achieved when the molecular weight of the polymer is high. One of the most suitable thermoplastic polymers used for these filters is High Density Polyethylene (HDPE) with a molecular weight approaching one million. So-called Ultra High Density Polyethylenes have molecular weights of one million or more and have melt indices of 0.0 to 0.5.

Any thermoplastic polymer meeting the desired low melt index conditions can be used for filter applications, including, without limitation, polypropylene, polyethylene, polysulfone, polyethersulfone, polyphenylene sulfide, ethylene vinyl acetate and the like. Typically, any thermoplastic polymer can be irradiated with either gamma rays or X-rays to induce cross-linking within it, which results in an increase in its molecular weight and which decreases its melt flow rate. Typically, sintered porous filters are made with predetermined particle size, which determines the size of its pores; i.e., the finer the size of the original particle, the finer is the average size of the pore in the sintered product. In fluid filtration applications, sintered filters have average pore sizes from 5 microns to 100 microns. The original size of the thermoplastic particle to produce these pore sizes in the filter is from 40 to 800 microns. More typically, the particle size is from 75 to 300 microns. Besides the size of the original particles, the porosity of the sintered filter can also be controlled by using blends of high and low melt flow materials. In this case, high melt polymers determine the average pore size, while the low melt polymer gives the filter its structural strength. Besides using blends of similar and dissimilar polymers with high and low melt flow rate, it is also possible to add other types of particulate materials in the matrix that impart other properties to the filter structure. For instance it is possible to embed activated carbon, synthetic ion exchange resins, inorganic and organic adsorption media such as metal oxides, modified peat, etc., in the sintered product (See EP Patent 0,659,482A1). The resultant filter then has the added capability to adsorb volatile organic substances such as pesticides, inorganic dissolved ions such as calcium, lead, mercury, arsenic and nitrates, etc., besides its traditional function to remove particulate materials.

Although the science and art of making sintered filters with various capabilities to remove particulate material and dissolved organic and inorganic impurities from fluid is well established, there is still a paucity of technology to protect these sintered porous filters from microbial growth. Trapped microorganisms are able to proliferate in these filters, creating serious health hazards, especially in the field of drinking water and where the filters are used in the processing of materials for human consumption such as food. The growth of microorganisms within the filter also reduces flow through the filter and requires higher operating pressures and/or frequent filter replacement. One of the technologies to prevent the growth of microorganism uses iodinated synthetic ion exchange resin embedded in sintered thermoplastic porous filter (See EP 0,659,482 A1"Ion exchange resin sintered in porous matrix" by Edward C. Giordano and Hans-Gunther Sternagel) Here antimicrobial action depends on slow release of iodine ions. While this method is acceptable to the U.S. Environmental Protection Agency (EPA) on a temporary or emergency basis to purify drinking water, its prolonged usage is not approved by the EPA because of the adverse effect of iodine on human health. In other known technology a synthetic ion exchange resin or other material such as activated carbon can be treated with silver and then subsequently embedded in the porous sintered thermoplastic filter. This method of treatment suffers from very high cost and also by the fact that silver surfaces become deactivated when exposed to water containing dissolved chlorine or chloride ions.

Applicant is aware of the following U.S. Patents and European Patent Office publications concerning the use of sintered porous filters made from thermoplastic materials.

| U.S. Pat. No. | Inventor | Issue Date | Title |
|---|---|---|---|
| 6,030,558 | Smith et al. | 02-29-2000 | Sintered Porous Plastic Products and Method of Making Same |
| 5,547,481 | Herding et al. | 08-20-1996 | Filter Element Having An Inherently Stable, Permeably Porous Plastic Body |
| 4,797,243 | Wolbrom | 01-10-1989 | Dye-Containing Porous Plastic Element and Method of Making It |

| EPO | Inventor | Pub. Date | Title |
|---|---|---|---|
| 0743085A2 | Takiguchi et al. | 11-20-1996 | Porous Plastic Filter and Process For Its Production |
| 0659482A1 | Giordano et al. | 06-28-1995 | Ion Exchange Resin Sintered In Porous Matrix |

SUMMARY OF THE INVENTION

The present invention provides an effective way to prevent the growth of microorganisms within a sintered porous filter by incorporating in it an antimicrobial agent that is practically insoluble in the fluid passing through the filter, and is safe, nontoxic, non-carcinogenic, non-sensitizing to human and animal skin, and does not accumulate in the human body when ingested. Furthermore this antimicrobial is a broad spectrum antimicrobial agent, i.e., it is equally effective against the majority of harmful bacteria encountered in water and food. For example, an antimicrobial agent such as 2,4,4'-trichloro-2'-hydroxydiphenol ether, or 5-chloro-2-phenol (2,4 dichlorophenoxy) commonly sold under the trademark Microban Additive B, by Microban Products Company, Huntersville, N.C., typically will be used. However, it will be understood that various other antimicrobial agents that are safe, non-toxic, and substantially insoluble in water or a fluid in question can be used in the present invention.

During normal operation, the antimicrobial agent is incorporated into a second thermoplastic material having an equal or higher melt flow rate than the first thermoplastic, but preferably a higher melt flow rate. Preferably, the porosity and the homogeneous distribution of antimicrobial agent is achieved by using blends of high and low melt flow material.

The present invention incorporates antimicrobial treatment of sintered porous thermoplastic filters used in purification of liquids, firstly to protect these filters from microbial growth within the filter (Bactriostasis), making it a source of added contamination, and secondly for the microbial treatment of liquids as they pass through these filters (Bacteriocidal). A unique feature of this invention is the achievement of the above objectives in a cost-effective manner using antimicrobial additives that do not pose any danger to human beings or to the environment.

The essence of this invention is a filter having porosity provided by the interstices between the particles, with an additional surface of thermoplastic particles on the basic particles, the additional surface of thermoplastic particles having an antimicrobial agent incorporated therein which in no way affects the sintering process that creates the matrix of porosity in the filter. The particles of the thermoplastic polymer are still able to melt and fuse at the point of contact during sintering, creating a stable rigid porous structure. This is achieved by introducing the antimicrobial agent as a concentrate in another chemically and physically compatible thermoplastic polymer that has substantially the same, but preferably higher, melt flow rate compared to the main thermoplastic polymer. Preferably, the melt flow rate of thermoplastic polymer containing homogeneously distributed antimicrobial additive is sufficiently high that it wets the surface of main thermoplastic particles and becomes uniformly distributed over the entire surface, except for the fused points of contact. Care must be exercised in choosing the difference between the melt flow rates so that the extreme differences in the flow properties do not lead to incomplete coverage of the particle surfaces with the antimicrobial additive. If there are extreme differences in the melting temperatures as well as in the melt flow rates of the two polymers, there will be separation of these polymers that will result in inhomogeneous and inconsistent distribution of antimicrobial additive within the porous structure.

A porous sintered filter produced under the optimum conditions of this invention creates a matrix of bonded solid particles and pores where the antimicrobial additive uniformly and substantially continuously covers the surfaces, although some gaps in coverage can be tolerated. By either choosing the particle size of the thermoplastic that is within the specified range or by combination of low and high melt flow polymers, it is possible to create a very tortuous path for the liquid flowing therethrough so that microorganisms are forced to encounter the antimicrobial surfaces during their path and become deactivated. Thus, even though the pores of these filters are greater than 5 micron, the filters are still effective in deactivating the much smaller microorganisms that pass through them. As a result, it is possible to treat water or other fluids through this filter to reduce the concentration of microorganisms by greater than 99%.

The invented sintered porous thermoplastic filter may have embedded therein materials such as activated carbon, synthetic ion exchange resins, inorganic media which adsorb perchlorates, nitrates, calcium, or heavy metals such as lead, mercury, arsenic, chromium, etc. Of special note is that the invented filter provides protection of activated carbon and synthetic ion exchange resins, which are otherwise prone to attack by bacteria, which would create high counts of bacteria in the filter and in the fluid effluent.

The antimicrobial additive is preferably 2,4,4'-trichloro-2'-hydroxydiphenol ether, or 5-chloro-2phenol(2,4 dichlorophenoxy), which is commonly manufactured and sold under the trademark MICROBAN Additive B, by Microban Products Company, Huntersville, N.C., or a combination of one or more equivalent antimicrobial agents that are insoluble in water or other fluid to be filtered. It is important that the antimicrobial agent not leach into the water or the fluid being filtered during the filtration process. The above-mentioned antimicrobial agents or equivalent ones that are insoluble in water, and are safe to use in drinking water and food related applications, can be used in this invention.

The preparation of concentrate of antimicrobial agent requires taking into consideration the thermoplastic properties of the main constituent of the porous sintered filter. Thermoplastic polymer for the concentrate of antimicrobial agent is chosen so that its melt flow index is greater than that of the main thermoplastic polymer, in order for the former to uniformly spread over all the surfaces of the sintered filter. In selecting these two thermoplastic polymers, consideration also must be given to their melting or softening temperatures, in case they are chemically dissimilar.

Typically a 10% to 20% concentrate by weight of the antimicrobial agent is prepared in the second thermoplastic polymer by a processing method such as: twin-screw extrusion, pelletizing and milling to size; or forming a mixture of a solution or emulsion of antimicrobial agent in a plasticizer. In order to ensure that this concentrate is homogeneously distributed in the mixture, its particle size is closely matched with that of the first thermoplastic polymer particles. The concentration of antimicrobial agent can be from 5% up to 80%, a preferable range is from 10% to 50%, but the optimum range of concentration is 10% to 20%. The let-down ratio of the concentrate into the main thermoplastic is determined by the concentration of the antimicrobial agent in the polymer concentrate and the concentration of the antimicrobial agent desired in the final sintered filter. Let-down ratios of from 1 to 1000, more typically 20 to 100, are used. A thermoplastic concentrate of additive such as this is diluted by addition of a preselected amount of primary thermoplastic polymer to achieve the final desired concentration of additive. Let-down ratio is the numerical value of dilution required to achieve the end concentration. A let-down ration of 20 would mean that one part of concentrate was diluted with 19 parts of primary thermoplastic polymer. Typically, the concentration of the antimicrobial additive based on the final weight of the sintered porous filter is in the range of approximately 50–20,000 ppm (parts per million) or 0.0005% to 2.0 percent by weight. Preferably a concentration of 1,000–5,000 ppm of antimicrobial additive is used, based on the weight of the final sintered porous filter, or 0.1 to 0.5 percent by weight.

The antimicrobial sintered porous filter of this invention can be used in the treatment of potable water. In many underdeveloped countries there is either a lack of infrastructure for municipally treated drinking water, or it exists in less than an adequate state. Under such conditions, it is necessary to have an over-head tank that is located on the roof of a building to store the water that is supplied, either intermittently by the municipalities, or by wells. Water in such tanks can become stagnant and subject to bacterial growth. It has now been found that the use of the antimicrobial sintered porous filter of this invention can eliminate the need to chlorinate the water and prevent the growth of bacteria in it. Simply by installing the invented filters on the outlet and inlet of the tank, drinking water was found to be devoid of detectable Coliform bacteria.

The antimicrobial sintered porous filter of this invention has also been used in water fount solutions for single or multi-station printing presses, either sheet or web fed, that use a water recirculation tank/system to filter/treat the recycled water. This water is subject to growth of bacteria and algae requiring frequent shut downs and clean ups. With the use of the invented filter this recycled water has been maintained free of microbial growth for very extended times such as 8 to 10 weeks, compared to less than one week before use of the invented filter.

A typical home or office humidifier draws ambient air and passes it through a moisture-laden wick filter and emits the resultant moist air back into the room or office. In these humidifiers, where water can be stagnant in some part of humidifier for extended periods, there can be the growth of undesirable bacteria such as *Legionella pneumophilia* and various types of algae. These microorganisms then can be emitted in the moist air causing serious danger to human respiratory health. The use of the invented antimicrobial sintered porous filter to treat the water to eliminate the bacteria before emitting it in the atmosphere can prevent aggravation of various allergies and respiratory diseases of human beings and animals, including pets.

Antimicrobial sintered porous filters of this invention can also be used in a spa. The current spa filter typically removes sediment from the water but is subject to severe microbiological growth. This necessitates addition and maintenance of high levels of chemical disinfectants such as chlorine. Use of antimicrobial sintered porous filters allows spa filters to avoid being a source of microbial growth and hence maintain more hygienic conditions in the spa filter and spa.

Water Coolers, where an inverted bottle sits atop a device that dispenses hot and/or cold water, are extensively used by commercial offices as well as by other consumers. Currently commercial filters are available that remove chlorine, taste and odor from the water contained in the bottle, using granulated activated carbon. The main disadvantage of such filter is the constant release of fine particulate carbon into the water and the growth of heterotrophic bacteria in the carbon, which creates bad taste in the water. The antimicrobial sintered porous filter of this invention overcomes both of these disadvantages as well as adding new features to this filter that were not possible before.

OBJECTS OF THE INVENTION

The principal object of the present invention is to provide an improved filter for purification of liquids.

Another object of this invention is to provide a method of making an antimicrobial sintered porous plastic filter.

Another object of this invention is to provide an antimicrobial sintered porous filter for filtration and purification of drinking water.

Another object of the invention is to provide apparatus for effective filtration and purification of water in a roof-top water storage tank, in printing presses, in spas, and in home and office humidifier and water cooler applications.

Another object of the invention is to provide a sintered porous thermoplastic filter for the treatment of fluids such as drinking water, fruit juices, oils, alcoholic beverages etc.

Another object of the invention is to provide a sintered porous thermoplastic filter for use in recirculation system of single or multi-station printing presses that are either sheet or web fed.

A further object of the invention is to provide a sintered porous thermoplastic filter for use in over-head rooftop water storage tanks to treat the water.

Another object of the invention is to provide a sintered porous thermoplastic filter for use in the treatment of water under gravity or pressure head of less than 10 psi.

Another object of the invention is to provide a sintered porous thermoplastic filter for use in the treatment of water under the pressure head of 10 to 500 psi.

Another object of the invention is to provide a sintered porous thermoplastic filter for use in air humidifiers.

BRIEF DESCRIPTION OF THE DRAWINGS

The foregoing and other objects will become more readily apparent by referring to the following detailed description and the appended drawings in which.

DETAILED DESCRIPTION

Figure 1:
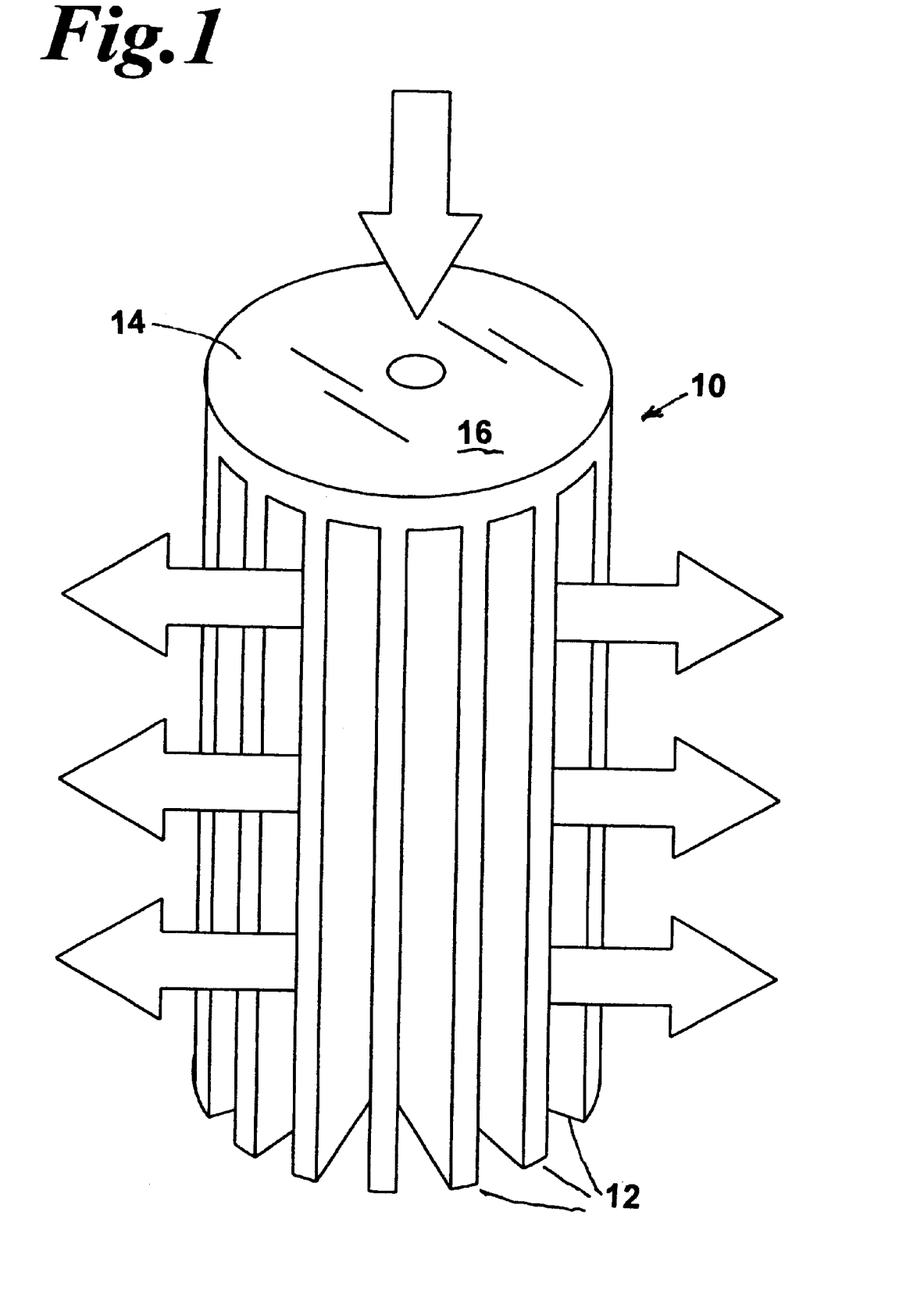
FIG. 1 is an isometric view of an antimicrobial sintered porous filter of this invention.

Referring now to FIG. 1, the invented antimicrobial sintered filter 10 is depicted in a usable form. The filter 10 is shown with a series of pleats 12, and an end cap 14. A similar end cap can be provided at the other end, if desired. In use, the liquid enters through the hole 16 in the end cap, passes through the interstices within the filter and then outward as indicated by the directional arrows, as the bottom of the filter is not open.

Figure 2:
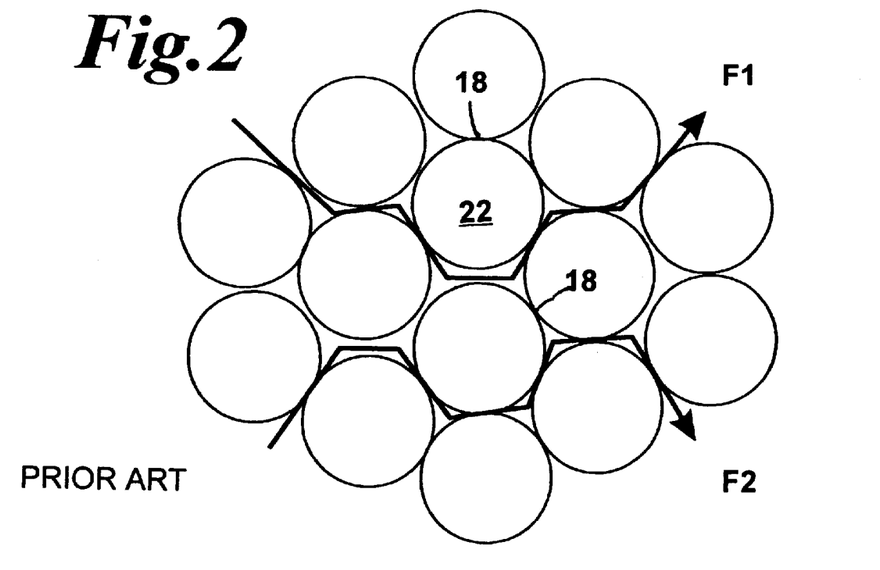
FIG. 2 is a schematic representation of thermoplastic particles in a sintered porous filter.

FIG. 2 shows magnified particles of a standard prior art filter, lines F1, F2 and arrows showing the path of the liquid as it flows through the filter and around the particles. As can be seen, the liquid follows a tortuous path.

Figure 3:
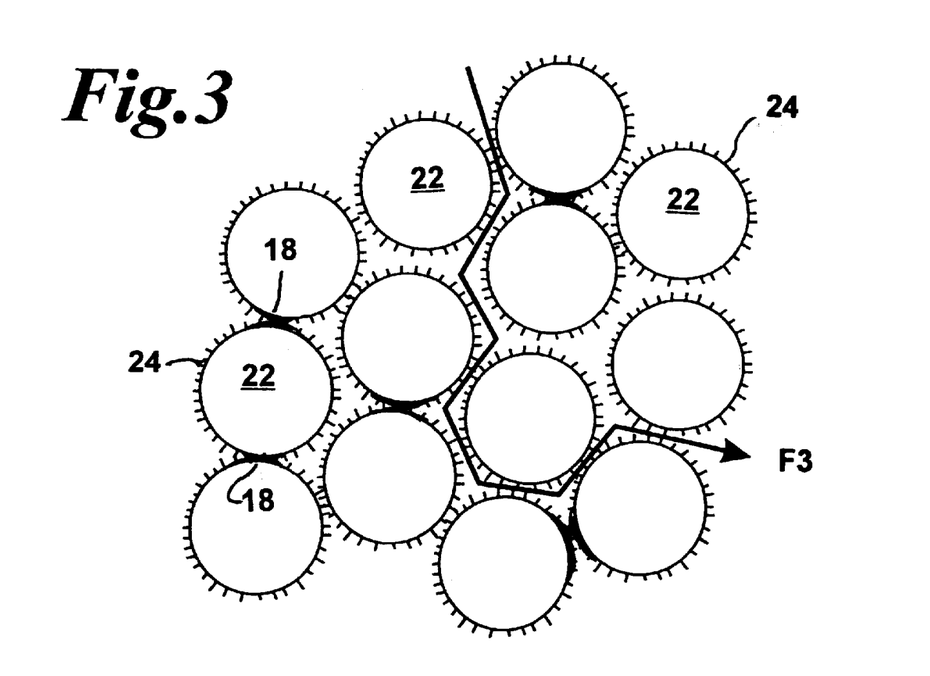
FIG. 3 is a schematic representation of the sintered porous thermoplastic filter treated with antimicrobial additive of this invention.

FIG. 3 is a schematic drawing showing the details of the invented filter 10 with the filter particles 22 magnified as in FIG. 2. The basic particles 22 are coated with a second plastic containing antimicrobial agent 24 on their outer surface. One possible fluid path through the filter is shown as F3.

Figure 4:
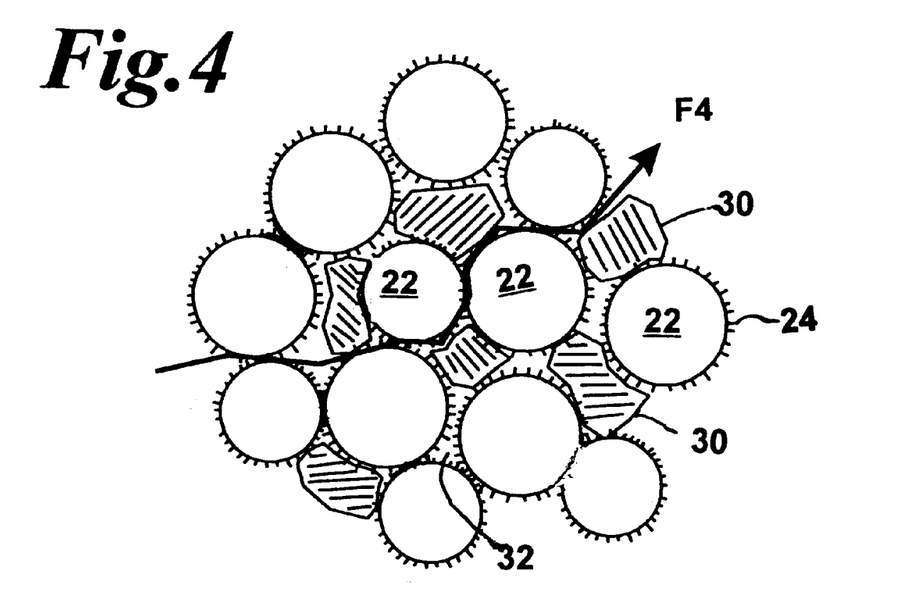
FIG. 4 is a schematic representation of activated carbon embedded in an antimicrobial sintered porous thermoplastic filter.

FIG. 4 depicts the inclusion of activated carbon particles 30 within the filter, still leaving sufficient interstices for the liquid to flow through the filter.

Figure 5:
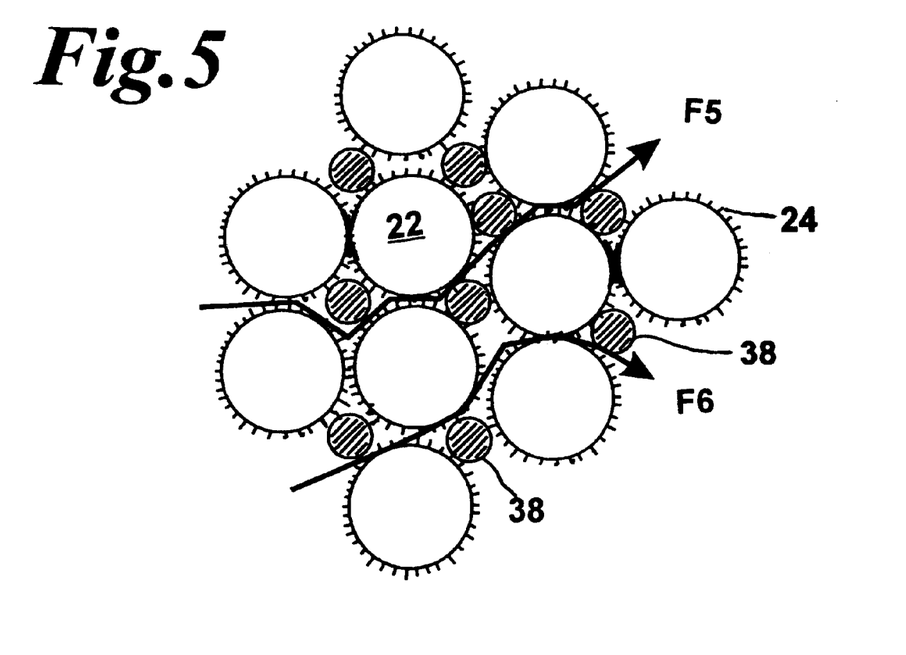
FIG. 5 is a schematic representation of a synthetic ion exchange resin embedded in an antimicrobial sintered porous thermoplastic filter.

Ion exchange resins 38 may be embedded in the interstices 32 of the filter as depicted in FIG. 5.

An antimicrobial sintered porous filter, as shown in FIG. 1, was made with High Density Polyethyene of Melt Flow Index of 2.0 (Test Method ASTM-D1238), which has a softening point range of 260 to 280 F. A 10% concentrate of antimicrobial agent, Microban Additive B, was prepared in a Low Density Polyethylene having a Melt Index of 25, using a twin-screw extruder, then pelletizing it and subsequently milling the pelletized particles to 30 mesh (about 500 micron). HDPE was milled to minus 60 to 200 mesh (260 to 75 micron) size. An intimate blend was prepared using 19 parts of powered HDPE and 1 part of powdered LDPE-Microban concentrate. The blended powder was molded in a mold of suitable design to produce the filter 10 shown in FIG. 1. The mold temperature was maintained in the range of 260–280 F. for 30 minutes or for sufficient time to fuse the particles at contact point 18 without melting them. After cooling the molded filter, a polyurethane end cap was applied to it, as shown. The finished filters were subjected to Standard Kirby Bauer Test to determine the antimicrobial efficacy. Tables 1–3 show the results. These results show that these filters are highly effective against both Gram positive (*S. aureus*) and Gram negative (*E. coli*) bacteria.

TABLE 1

MICROBIOLOGICAL TEST RESULTS
KIRBY BAUER TEST METHOD

| Test Organism: | *Staphylococcus aureus* ATCC 6538 |
| --- | --- |
| | *Escherichia coli* ATCC 25922 |
| Sample Material: | HDPE |
| Sample Size: | 20 mm square |
| Growth Medium: | Mueller-Hinton Agar |
| Test Conditions: | Incubated at 37° C. ± 2° C. for 18–24 hours |

| | Results (Zone Size) | |
| --- | --- | --- |
| Sample Identification | *S. aureus* | *E. coli* |
| 2385-#573 Control | NZ/I | NZ/NI |
| 2386-#574 | 18 mm | 9 mm |
| 2387-#575 | 16 mm | 6 mm |

Interpretation of Results
NZ = No Zone of inhibition surrounding the sample
NI = No Inhibition of Growth Under the Sample
I = Inhibition of Growth Under the Sample (If Observable)
mm = Zone of Inhibition Reported in Millimeters

TABLE 2

MICROBIOLOGICAL TEST RESULTS
KIRBY BAUER TEST METHOD

| Test Organism: | *Staphylococcus aureus* ATCC 6538 |
| --- | --- |
| | *Escherichia coli* ATCC 25922 |
| Sample Material: | PE |
| Sample Size: | 20 mm square |
| Growlh Medium: | Mueller-Hinton Agar |
| Test Conditions: | Incubated at 37° C.~2° C. for 18–24 hours |

| | Results (Zone Size) | |
| --- | --- | --- |
| Sample Identification | *So aureus* | *E. coli* |
| 2428-Sintered Filter (XM1917 Run) | 20 mm | 11 mm |
| Duplicate | 21 mm | 11 mm |

Interpretation of Results
NZ = No Zone of inhibition surrounding the sample
NI = No Inhibition of Growth Under the Sample
I = Inhibition of Growth Under the Sample (If Observable)
mm = Zone of Inhibition Reported in Millimeters

TABLE 3

MICROBIOLOGICAL TEST RESULTS
KIRBY BAUER TEST METHOD

| Test Organism: | *Staphylococcus aureus* ATCC 6538 |
| --- | --- |
| | *Eseherichia coli* ATCC 25922 |

TABLE 3-continued

MICROBIOLOGICAL TEST RESULTS
KIRBY BAUER TEST METHOD

Sample Material: PE
Sample Size: 20 mm square
Growth Medium: Mueller-Hinton Agar
Test Conditions: Incubated at 37° C. ± 2° C. for 18–24 hours

| Sample Identification | Results (Zone Size) | |
|---|---|---|
| | S. aureus | E. coli |
| 2507-00726A-1 Sintered Filter | 15 mm | 14 mm |
| 2508-00726A-2 Sintered Filter | 16 mm | 14 mm |
| 2509-00801A Sintered Filter | 16 mm | 14 mm |

Interpretation of Results:
NZ = No Zone of inhibition surrounding the sample
NI = No Inhibition of Growth Under the Sample
I = Inhibition of Growth Under the Sample (If Observable)
mm = Zone of Inhibition Reported in Millimeters Table 4 shows that both the preblends and the sintered filters have more than 3000 ppm of Microban Additive B with one time extraction with methanol.

TABLE 4

ANALYTICAL TEST RESULTS
EXTRACTION TEST METHOD

Sample. Material: PE preblend

| Sample Identification. | Sample Weight (g) | Extracted Amount of Microban (ppm) |
|---|---|---|
| A473-PE preblend, | 1.0013 | 3800 |
| A474-PE preblend, | 1.0032 | 3600 |
| A475-Sintered top | 1.0006 | 3200 |
| A476-Sintered bottom | 1.0004 | 3200 |

The extracted amount of Microban shown above was determined by converting the average peak area from the HPLC chromatograms into the concentration of Microban in the extract. This was done by first analyzing a series of calibration solutions containing known amounts of Microban and plotting their peak areas versus their respective-concentrations. The linear regression formula from this plot was used to convert the average peak area of the subsequent sample extract to its respective concentration unit. This concentration was converted to a part per million value by multiplying by the extraction volume and dividing by the sample weight.
Note: Samples A475 and A476 were cryomilled prior to extraction.

Figure 6:
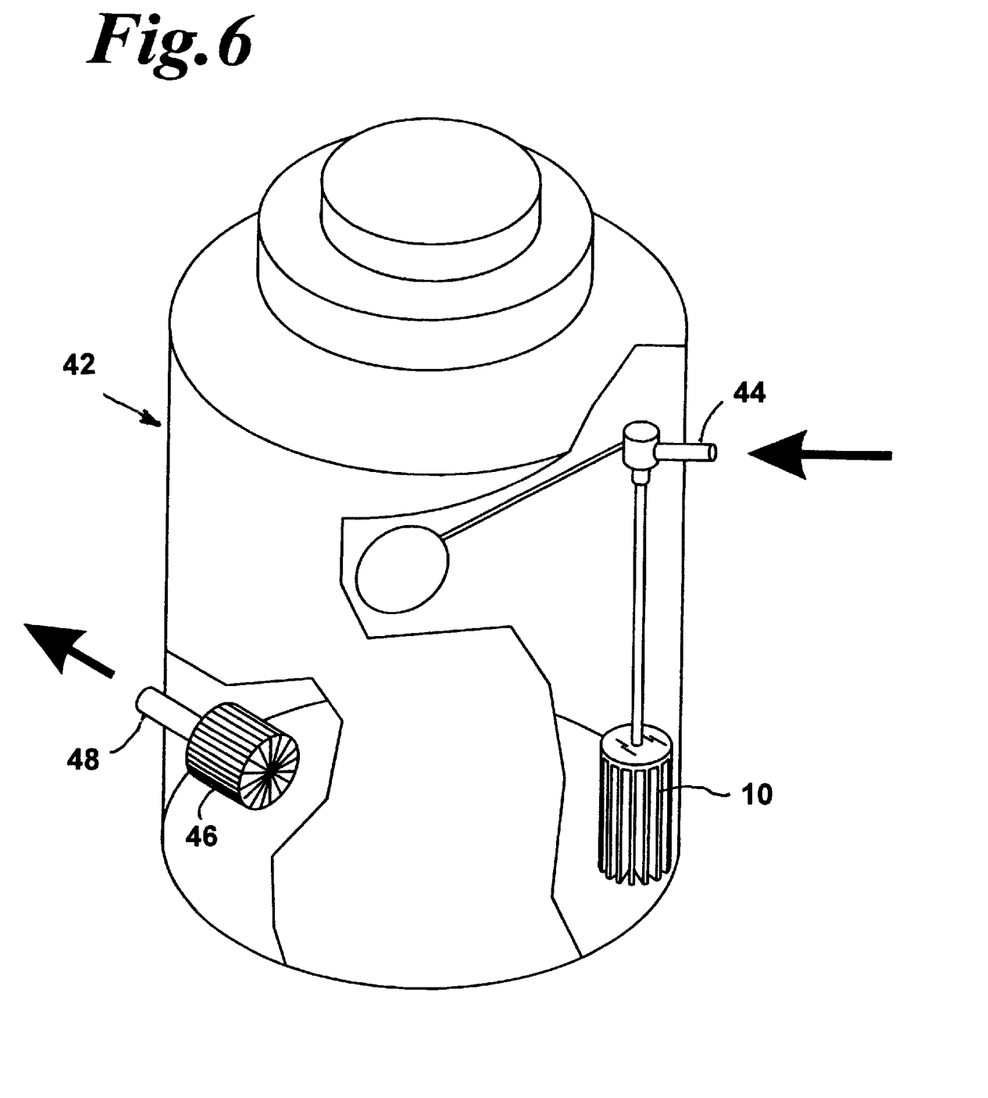
FIG. 6 is a schematic cross-section of an overhead rooftop water storage tank fitted with both inlet and outlet antimicrobial sintered porous filters of this invention.

A sintered porous HDPE filter was installed both at the inlet and outlet of a Roof-Top water storage tank as shown in FIG. 6. Tank 42 has a water entry 44 connected to a filter 10. A similar filter 46 is provided at the exit 48 of the tank. Both the incoming and outgoing water were monitored for a one-week period for both Total Coliform and Fecal Colifom bacteria by conventional means. While incoming concentrations of these bacteria was in the range of 1000 to 5000 CFU (Colony forming units) per ml, the outgoing concentrations at all times were undetectable.

In both single and multi-station printing presses, the fount solution is recirculated. Under normal conditions this fount solution develops significant growth of bacteria and algae within a week. The recirculation tank and solution distribution lines then have to be cleaned to maintain the quality of printing on inked and non-inked surfaces of the printing plate satisfactory. By installing invented antimicrobial sintered porous HDPE filter in the recirculation loop, a printing press can be run continuously at least for 10 weeks without any interruption.

Figure 7:
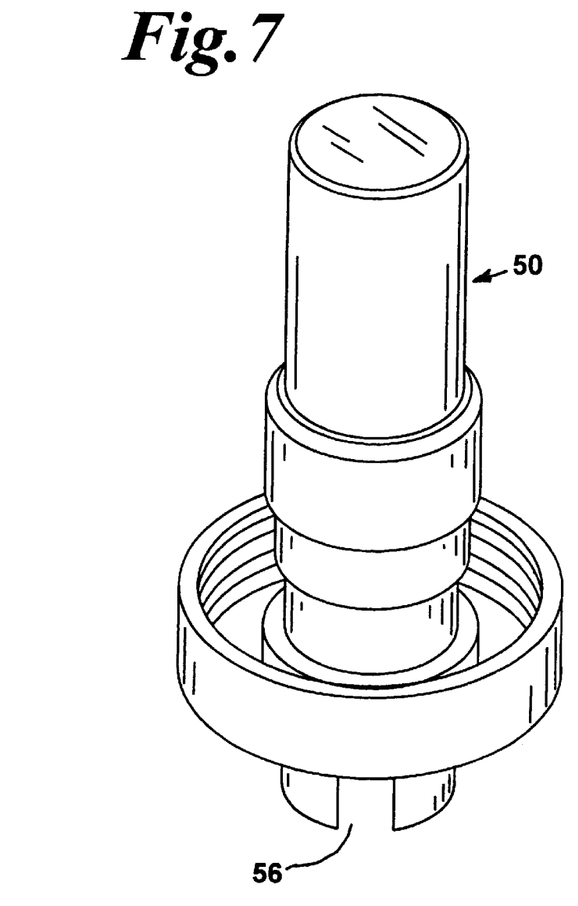
FIG. 7 is a diagram of humidifier filter holder, a coupler and a closed end antimicrobial sintered porous filter.
Figure 8:
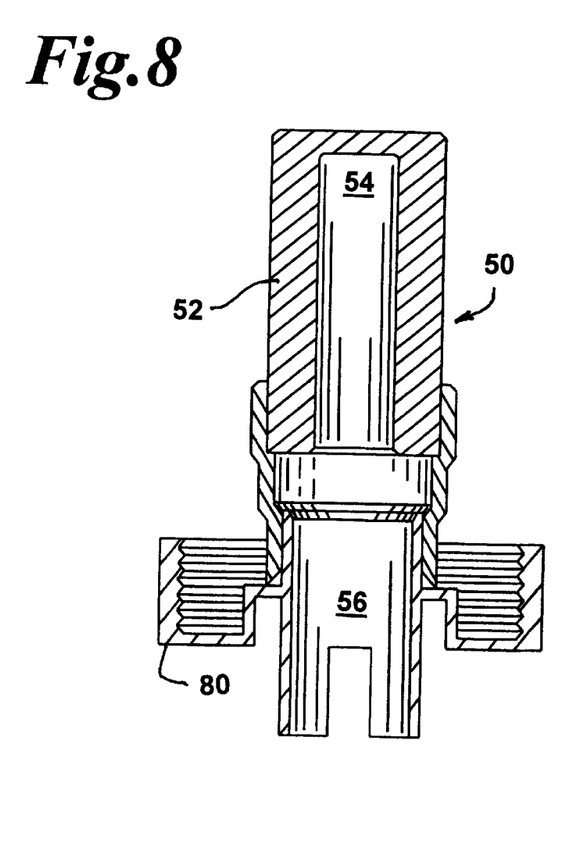
FIG. 8 is a diagram of humidifier filter holder, a coupler and a closed end antimicrobial sintered porous filter.

FIGS. 7 and 8 show the invented filter 10 as a candle type filter 50 which has a sintered porous solid portion 52 surrounding an open center 54. Liquid flows into the filter through the sides and top of the filter and is withdrawn through the bottom 56.

Figure 9:
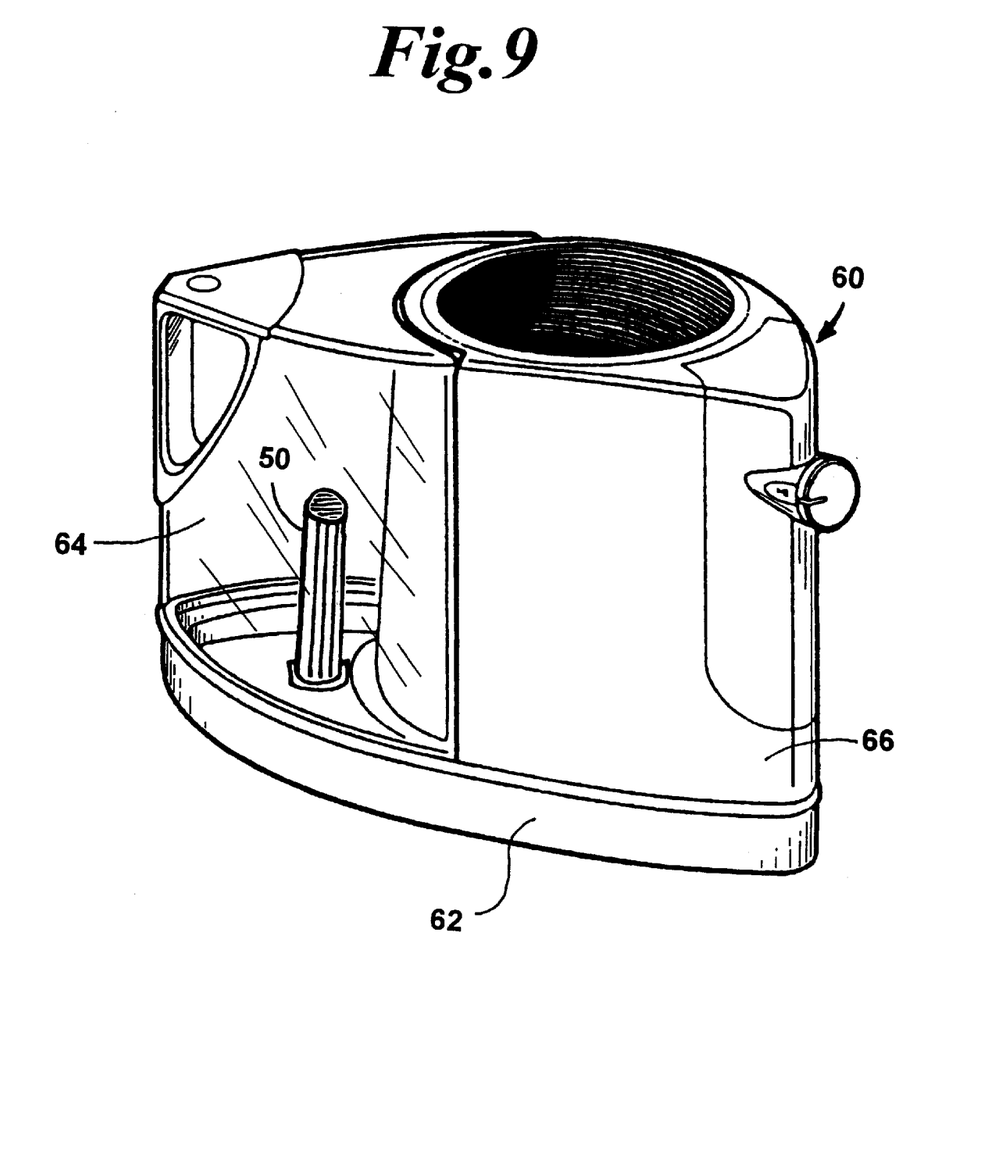
FIG. 9 is a partially cut away isometric view of a humidifier with an antimicrobial sintered porous filter.

FIG. 9 shows the invented filter installed in a typical home or office humidifier. This filter is shown as pleated as in FIG. 1, but it could also be a candle style filter such as shown in FIGS. 7 and 8.

As shown in FIG. 9, a humidifier 60 has a base 62 which supports a water tank 64 and humidifier housing 66. Such a humidifier water tank 64 is designed to be lifted from the base 62 and filled with water by removing a tank cap 80 located at the bottom of the tank. A spring loaded mechanism 68 in or associated with the cap 80 acts as a one way valve in the trough 70 of the base which maintains a constant level of water in the trough which keeps wicking filter 72 moist at all times. Wicking filter 72 is positioned over a pedestal 74. A standing water level is maintained in the trough 70, which keeps the tubular wicking filter 72 wet. During operation, air is drawn through an air intake grill area located in the humidifier base, passes through moisture-laden wicking filter 72 and the damp air is directed into the room from the top of the humidifier.

Figure 10:
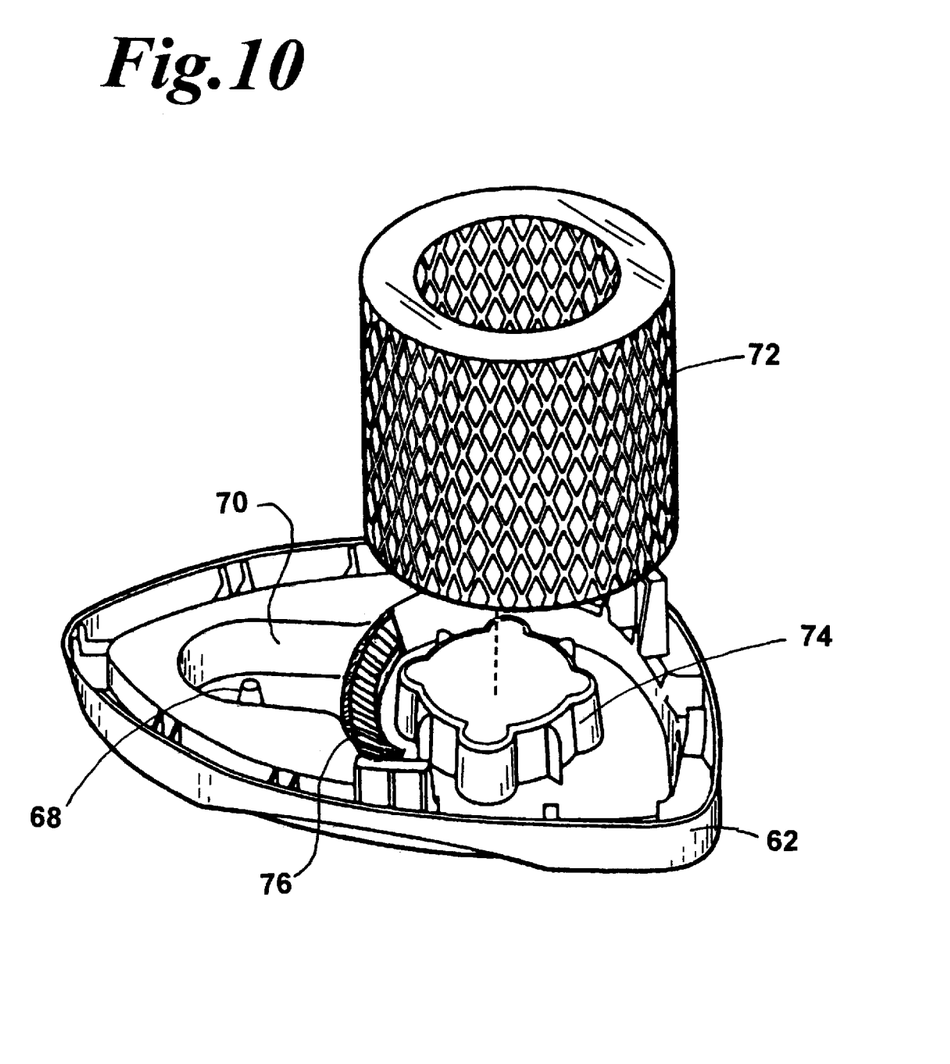
FIG. 10 is a partially exploded isometric view of a humidifier base with an antimicrobial sintered porous dam filter.

An antimicrobial sintered porous ethylene vinyl acetate filter in the humidifier prevents the growth of microorganisms in the water, and softens the water by removing hardness-causing ions such as calcium and magnesium from it. This ensures that dangerous bacteria are not present in the moisture that is directed into the room and no mineral deposits are left on the wicking filter and the internal parts of the humidifier base. Preferably, two types of filters are used in this application. One is a candle type closed end filter that engages the twist off cap 80 of the humidifier water tank located at the tank bottom, and the other is a dam filter 76 located in the trough adjacent the wicking filter 72 as shown in FIG. 10.

Ethylene vinyl acetate (EVA) polymer with a Melt Index of 6 was selected as a main constituent of both the candle filter 50 and the curved dam filter 76. The particle size of the filters in this case was from 60 mesh to 200 mesh (250 to 75 micron). Another EVA polymer with a Melt Index of 10 was chosen for the preparation of 10% Microban Additive B concentrate, which was milled to powders from 60 mesh to 200 mesh. A blend of these powders was prepared with 16 parts of main EVA and 1 part of EVA containing Microban Additive B. To this blend was added 4 parts by weight of strong acid cation exchange resin made up of polystyrene cross-linked with divinyl benzene with sodium as the original cation and having a particle size of 40 to 60 mesh. The blended powders with the synthetic ion exchange resin were again thoroughly mixed, were put into appropriate molds, and sintered at 275–300 F. for 15 to 20 minutes or for sufficient time to fuse the particles without melting them. The cooled candle filter 50 was mounted on the twist off tank cap with a coupler (see FIG. 8) and was installed in the humidifier water tank. Similarly, the curved dam filter 76 was installed in the trough of the humidifier base as shown in FIG. 10.

For a period of 2 weeks, about 2 gallons per day of water containing 10,000 CFU/ml of *Klebsiella pneumonia* as a surrogate bacteria was put through the humidifier. Water samples were drawn from underneath the wicking filter (from the right hand side of the dam filter, as shown in FIG. 10) and analyzed for the bacteria. No viable bacteria were detected during the course of the trial. No mineral deposits were also found on the wicking filter at the end of this trial.

Figure 11:
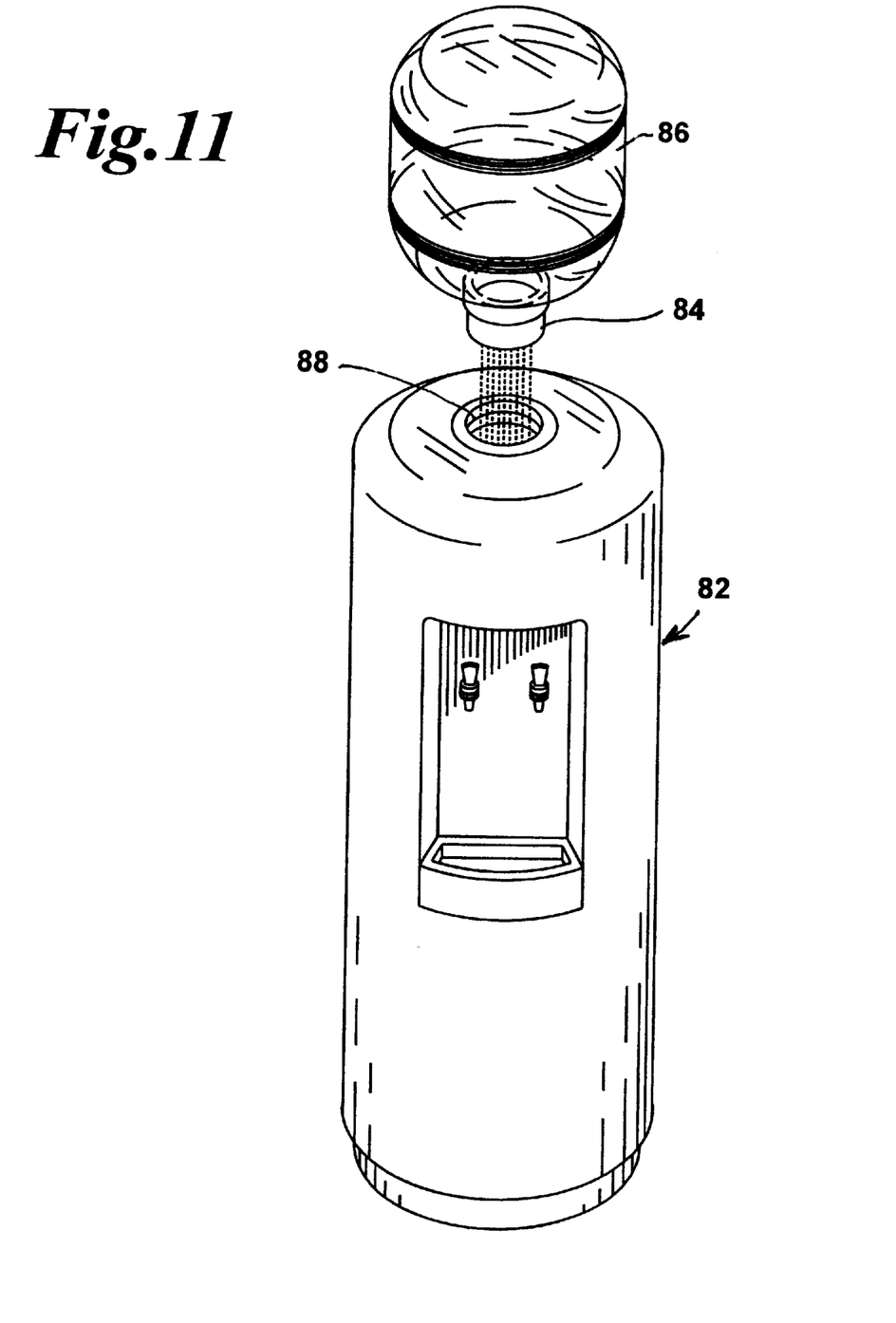
FIG. 11 is an isometric view of a water cooler with an antimicrobial sintered porous filter incorporated therein.

FIG. 11 shows a water dispenser, i.e. a typical office water cooler 82, which utilizes a disc filter 84 at the end of a water bottle 86 which is inserted into the reservoir 88 of the water cooler for use as a gravity filter. A disc shaped sintered porous filter, about 4 inches in diameter and 1½ inches thick, was created to fit the housing of the water filter that can be screwed on to the mouth of the water bottle 86 as shown in FIG. 11. The filter can be adapted for use in several ways, for instance, it can fit over the mouth of the water bottle 86, or it can fit into the opening of the reservoir 88.

A blend of powdered EVA (Melt Index-6; 60–200 mesh), Microban Additive B concentrate in EVA (Melt Index-10; particle size-60–200 mesh), styrene-divinyl benzene based synthetic cation and anion exchange resins (60–100 mesh) and activated carbon made from coconut shell (−100 mesh), was prepared as follows:

- 40 parts-EVA-Melt Index-6; Particle size −60 to +200 mesh.
- 5 parts-Microban/EVA concentrate-Melt Index-10; Particle size −60 to +200 mesh.
- 40 parts-Coconut-Activated Carbon; Particle size −100 mesh.
- 10 parts-Cation Exchange Resin; Particle size 60 to 100 mesh.
- 10 parts-Anion Exchange Resin; Particle size 60 to 100 mesh.

All the powders were thoroughly mixed, put into a disc-shaped mold and sintered at 275 to 300 F. for 15 to 20 minutes to allow softening of EVA particles and bring about bonding between all the particles. The resultant disc-shaped sintered filter 84 was mounted in the filter housing shown in FIG. 11 and tested with the following results:

1) It prevented the growth of bacteria within the filter;
2) It removed over 99% of bacteria from the water (Coliform);
3) It removed chlorine, taste and odor;
4) It removed dissolved lead, mercury, copper chromium and zinc;
5) It removed dissolved arsenic and nitrates;
6) It did not have any fine carbon particle emissions in the water;
7) It removed over 99% of Cryptosporidium.

Currently spas have a pleated nonwoven polyester filter that is mounted on a porous plastic core with appropriate polyurethane end caps to fit the housing mounted in the spa. The purpose of this filter is to remove sediment from the circulating water. The disadvantage of this filter is the accumulation and growth of microorganisms on this filter in the presence of organic and inorganic sediments which are caught on this filter, resulting in microbiological fouling. It has been found that protection of this filter from microbial growth can be achieved by substituting a sintered porous plastic core incorporating Microban antimicrobial agent at 0.1% to 0.5% concentration and synthetic Cation ion exchange resin at 20 to 30% concentration, based on the final weight of the filter. Alternatively, a complete pleated filter (as shown in FIG. 1) of sintered porous plastic that fits the existing spa housing using the same concentrations of Microban and a synthetic Cation exchange capacity can be utilized in a spa. Such a filter is capable of removing hardness causing ions such as calcium, magnesium and soluble iron, copper, zinc, tin, etc., which cause staining, while protecting the filter from microbial growth. This promotes better flow rates and inhibits microbiological fouling.

SUMMARY OF THE ACHIEVEMENT OF THE OBJECTS OF THE INVENTION

From the foregoing, it is readily apparent that I have invented an improved sintered porous thermoplastic filter for the purification of liquids, which incorporates a non-leaching antimicrobial agent, improved apparatus for effective filtration and purification of water in a roof-top water storage tank, a humidifier, or a water cooler, and a method for making an improved sintered porous thermoplastic filter for the purification of liquids which is more effective than heretofore has been possible.

It is to be understood that the foregoing description and specific embodiments are merely illustrative of the best mode of the invention and the principles thereof, and that various modifications and additions may be made to the apparatus by those skilled in the art, without departing from the spirit and scope of this invention, which is therefore understood to be limited only by the scope of the appended claims.

What is claimed is:

1. A filter for the purification of liquids, comprising:
    thermoplastic particles of preselected size sintered to form a porous thermoplastic mass having interstices therein;
    said thermoplastic mass being coated by a second thermoplastic with a non-leaching antimicrobial agent incorporated therein.

2. A sintered porous thermoplastic filter according to claim 1 wherein said antimicrobial agent is selected from the group consisting of 2,4,4'-trichloro-2-hydroxy diphenol ether and 5-chloro -2phenol(2,4 dichlorophenoxy) compounds.

3. A sintered porous thermoplastic filter according of claim 1, wherein said thermoplastic particles include particles of one major thermoplastic polymer A and particles of a second thermoplastic polymer B which contain a concentrate of antimicrobial agent.

4. A sintered porous thermoplastic filter according to claim 3, where thermoplastic polymer B has a melt index equal to or greater than the melt index of thermoplastic polymer A.

5. A sintered porous thermoplastic filter according to claim 1 wherein the concentration of antimicrobial agent is from 50 to 20,000 parts per million.

6. A sintered porous thermoplastic filter according to claim 1, further comprising particulate material embedded therein.

7. A sintered porous thermoplastic filter according to claim 6, where said particulate material embedded in the filter is selected from the group consisting of: activated carbon, synthetic ion exchange resins, inorganic media having perchlorate, nitrate, lead, mercury, arsenic or chromium adsorptive properties, organic media having pesticide adsorptive properties, pigments, dyes, and mixtures thereof.

8. A sintered porous thermoplastic filter according to claim 4, further comprising at least one additional thermoplastic polymer incorporated therein to control the porosity of the filter.

9. A sintered porous thermoplastic filter according to claim 1 further comprising at least one end cap.

10. A sintered porous thermoplastic filter according to claim 9, wherein said end cap is selected from the group of plastics consisting of polyurethane, polypropylene, thermoplastic, or thermoset.

* * * * *